United States Patent
Keizer et al.

(10) Patent No.: US 7,233,826 B2
(45) Date of Patent: Jun. 19, 2007

(54) BI-VENTRICULAR AND SINGLE-VENTRICLE PACING

(75) Inventors: Diederick M. Keizer, Elst (NL); Peter Oosterhoff, Zutphen (NL); Mattias Rouw, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 664 days.

(21) Appl. No.: 10/424,582

(22) Filed: Apr. 25, 2003

(65) Prior Publication Data
US 2004/0215256 A1 Oct. 28, 2004

(51) Int. Cl.
*A61N 1/365* (2006.01)

(52) U.S. Cl. ....................................................... 607/28
(58) Field of Classification Search .................. 607/9, 607/15, 27–28
See application file for complete search history.

(56) References Cited

U.S. PATENT DOCUMENTS

| | | | |
|---|---|---|---|
| 5,534,018 A * | 7/1996 | Wahlstrand et al. .......... 607/27 |
| 5,720,768 A * | 2/1998 | Verboven-Nelissen ......... 607/9 |
| 5,741,312 A | 4/1998 | Vonk et al. |
| 5,902,324 A * | 5/1999 | Thompson et al. ............ 607/9 |
| 5,944,743 A | 8/1999 | Janssens |
| 6,016,447 A | 1/2000 | Juran et al. |
| 6,070,101 A | 5/2000 | Struble et al. |
| 6,081,748 A | 6/2000 | Struble et al. |
| 6,122,545 A | 9/2000 | Struble et al. |
| 6,148,234 A | 11/2000 | Struble |
| 6,456,878 B1 | 9/2002 | Yerich et al. ................... 607/9 |
| 6,493,586 B1 * | 12/2002 | Stahmann et al. ............ 607/27 |
| 6,922,589 B2 * | 7/2005 | Stahmann et al. ............ 607/27 |
| 6,937,901 B2 * | 8/2005 | Zhu et al. ..................... 607/27 |
| 2001/0012953 A1 | 8/2001 | Molin et al. ................... 607/9 |
| 2001/0049542 A1 | 12/2001 | Florio et al. ................... 607/9 |
| 2001/0049543 A1 * | 12/2001 | Kroll .............................. 607/28 |
| 2002/0082660 A1 | 6/2002 | Levine ........................ 607/14 |
| 2002/0151934 A1 | 10/2002 | Levine .......................... 607/9 |

OTHER PUBLICATIONS

Geelen et al., "Ventricular Fibrillation and Sudden Death After Radiofrequency Catheter Ablation of the Atrioventricular Junction," PACE, vol. 20, Feb. 1997, Part I, pp. 343-348.

* cited by examiner

*Primary Examiner*—George R. Evanisko
*Assistant Examiner*—Stephanie R Smith
(74) *Attorney, Agent, or Firm*—Daniel G. Chapik; Girma Wolde-Michael (57) ABSTRACT

The invention is directed to methods and apparatus for automatically changing from bi-ventricular pacing, in which an implantable medical device (IMD) applies pacing stimuli to both ventricles of a heart during a cardiac cycle, to single-ventricle pacing, in which the IMD paces one ventricle and inhibits pacing of the other. An IMD applying the techniques of the invention automatically changes from bi-ventricular pacing to single-ventricle pacing, or vice versa, as a function of the reliability of left ventricular pacing. Exemplary techniques for determining the reliability of left ventricular pacing include impedance measurement, capture testing, capture threshold testing, or any combination thereof.

35 Claims, 7 Drawing Sheets

BI-VENTRICULAR AND SINGLE-VENTRICLE PACING

FIELD OF THE INVENTION

The invention relates to cardiac pacing systems, and in particular, cardiac pacing systems capable of providing bi-ventricular pacing.

BACKGROUND OF THE INVENTION

Some patients receive an implantable medical device (IMD), such as a pacemaker, that is capable of applying pacing stimuli to the left ventricle of the heart, or to the right ventricle, or to both ventricles. Pacing both ventricles during a cardiac cycle, a technique known as "bi-ventricular pacing," may be useful for treating inter—and/or intraventricular electrical-mechanical dysynchrony. In some patients, however, pacing the left ventricle alone may be as beneficial as bi-ventricular pacing, or perhaps more beneficial than bi-ventricular pacing.

When a patient first receives an IMD that can perform bi-ventricular pacing, the physician for the patient typically enables bi-ventricular pacing, causing the IMD to pace both ventricles. Bi-ventricular pacing is often seen as a safety measure. In the event of failure or dislodgement of the left ventricular pacing lead, pacing only the left ventricle may result in a failure of pacing to "capture" the ventricles, i.e., to cause the ventricles to activate. Left ventricular pacing that fails to activate the ventricles does not help the patient. Because of considerations such as these, physicians are hesitant to rely on left ventricular pacing, and may program the IMD to apply bi-ventricular pacing.

BRIEF SUMMARY OF THE INVENTION

In general, the invention is directed to methods and apparatus for automatically changing from bi-ventricular pacing to single-ventricle pacing. "Single-ventricle pacing" as used herein comprises pacing one ventricle on a cardiac cycle and inhibiting pacing of the other ventricle on the same cardiac cycle. Single-ventricle pacing includes, but is not limited to, left ventricular pacing, which involves pacing the left ventricle while inhibiting pacing of the right ventricle. The invention also encompasses methods and apparatus for automatically changing from single-ventricle pacing to bi-ventricular pacing.

An IMD applying the techniques of the invention automatically changes from bi-ventricular pacing to single-ventricle pacing, or vice versa, as a function of the reliability of left ventricular (LV) pacing. When LV pacing is reliable, the IMD changes from bi-ventricular pacing to single-ventricle pacing, pacing only the left ventricle. The IMD continues to monitor whether LV pacing is reliable, and may change to bi-ventricular pacing or right ventricular (RV) pacing when LV pacing is unreliable.

The invention is not limited to any particular techniques for determining the reliability of LV pacing, but three techniques for determining the reliability of LV pacing are described herein. In particular, an IMD may employ impedance measurement, capture testing, capture threshold testing, or any combination thereof to determine the reliability of LV pacing.

In one embodiment, the invention is directed to a method comprising pacing a left ventricle in a first cardiac cycle and pacing a right ventricle in the first cardiac cycle, determining whether the pacing of the left ventricle is reliable in the first cardiac cycle, and pacing the left ventricle in a second cardiac cycle and inhibiting pacing of the right ventricle in the second cardiac cycle when the pacing of the left ventricle is determined to be reliable. The method may include further testing of the reliability of the pacing of the left ventricle, and may include resuming pacing of right ventricle when the pacing of the left ventricle is determined to be unreliable.

In another embodiment, the invention presents a method comprising pacing a left ventricle in a first cardiac cycle and inhibiting pacing of a right ventricle in the first cardiac cycle, determining whether pacing of the left ventricle is reliable in the first cardiac cycle, and pacing the right ventricle in a second cardiac cycle when the pacing of the left ventricle is determined to be unreliable. In the second cardiac cycle, the left ventricle may be paced as well, or pacing of the left ventricle may be inhibited. The method may include further testing of the reliability of the pacing of the left ventricle, and may include resuming pacing the left ventricle and inhibiting pacing of the right ventricle when the pacing of the left ventricle is determined to be reliable.

In further embodiments, the invention is directed to a computer-readable medium containing instructions that cause a programmable processor to carry out any of these methods.

In an added embodiment, the invention is directed to a device comprising a left ventricular lead having at least one left ventricular electrode, a right ventricular lead having at least one right ventricular electrode, a pulse generator to generate at least one pacing stimulus to pace at the left ventricle or the right ventricle or both ventricles, and a processor to determine whether a pacing of the left ventricle is reliable and to control the pulse generator to apply one of bi-ventricular pacing and single-ventricle pacing as a function of the determination.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
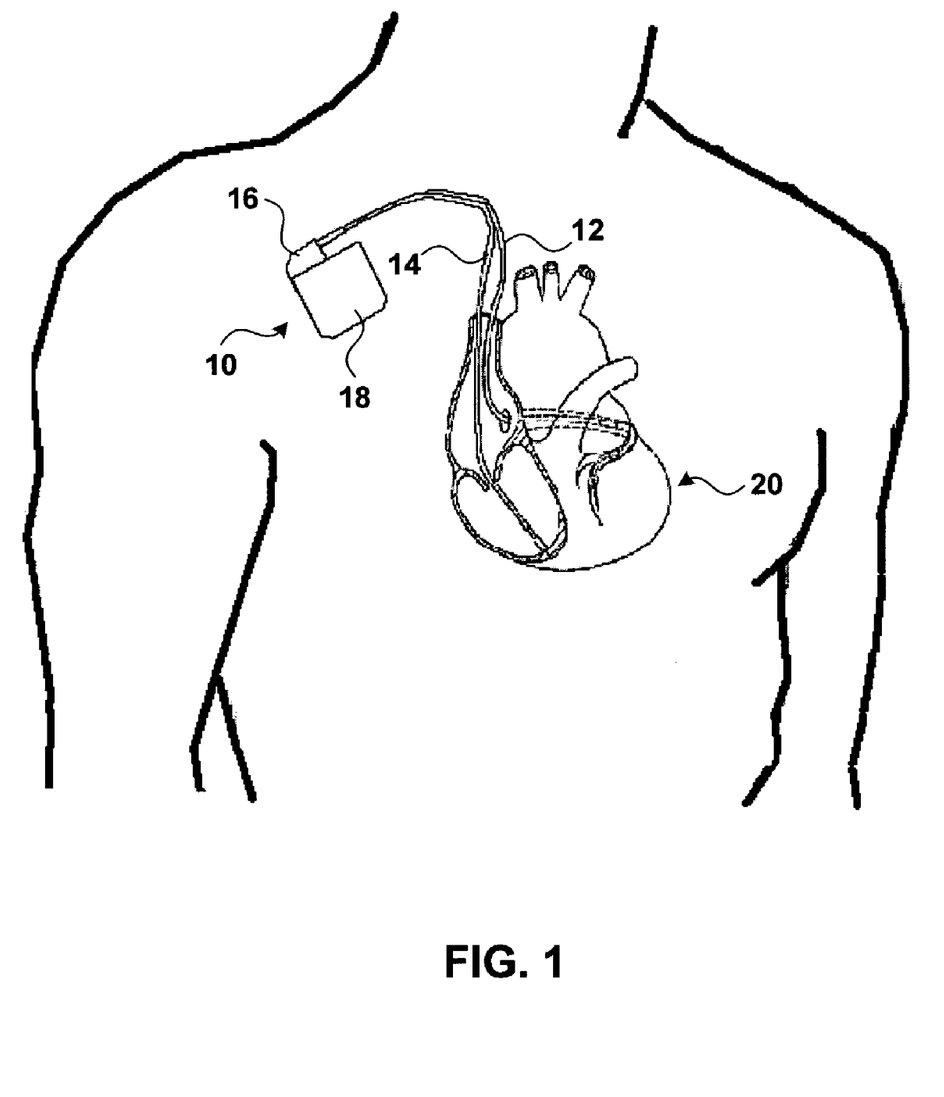
FIG. 1 is a schematic view of an exemplary implantable medical device capable of applying bi-ventricular pacing or single-ventricle pacing.

FIG. 1 is a schematic view of one embodiment of an implantable medical device (IMD) 10 that practices the invention. IMD 10 shown in FIG. 1 is a pacemaker coupled to at least one left ventricular pacing (LV) and sensing lead 12 and one right ventricular (RV) pacing and sensing lead 14. Pacing and sensing leads 12, 14 are attached to connector module 16 of hermetically sealed housing 18 and implanted near human or mammalian heart 20. Pacing and sensing leads 12, 14 sense electrical signals attendant to the depolarization and repolarization of heart 20, and further provide pacing pulses for causing depolarization of cardiac tissue in the vicinity of the distal ends thereof. Leads 12, 14 may have unipolar or bipolar electrodes disposed thereon.

Figure 2:
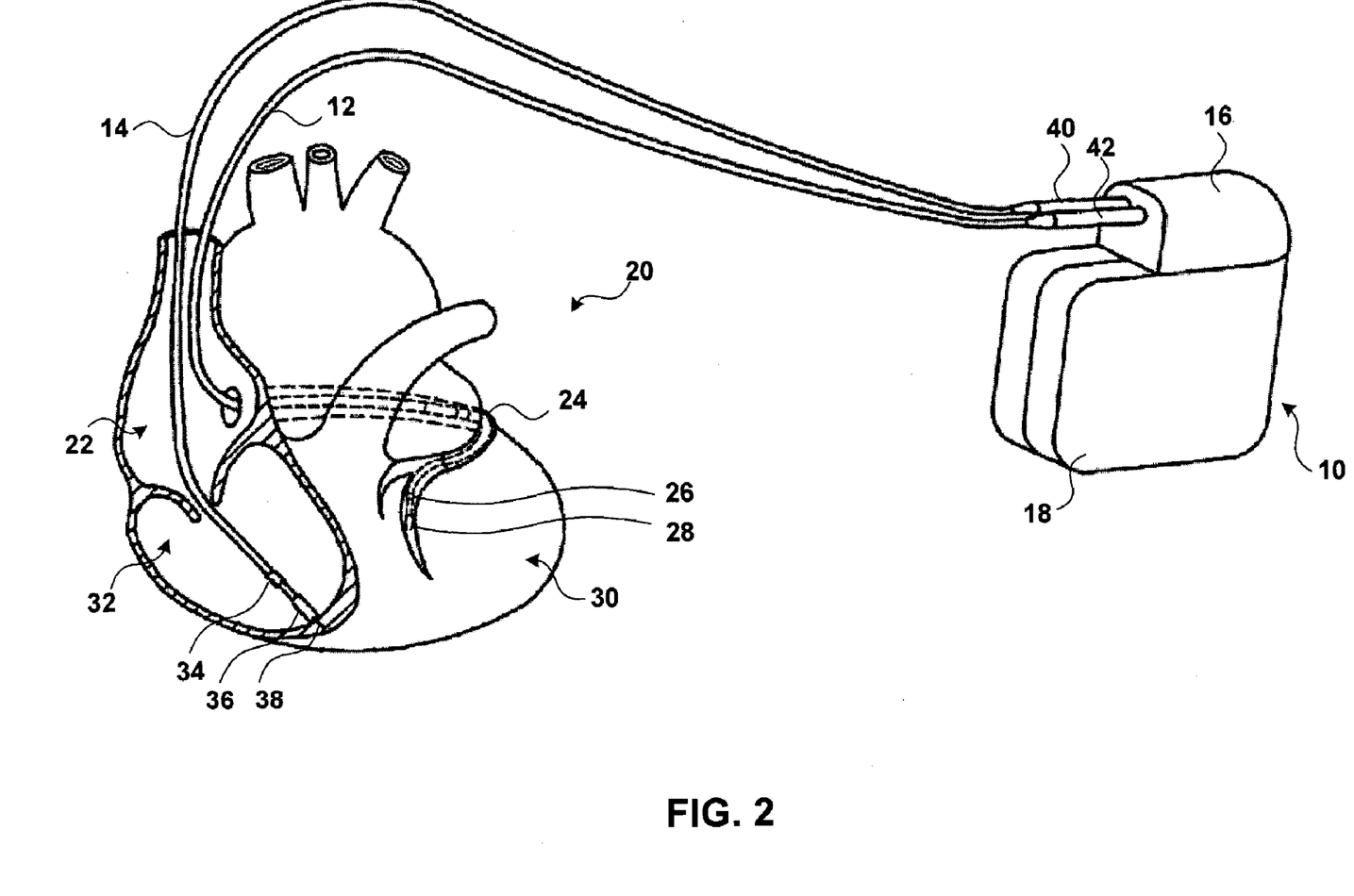
FIG. 2 shows the exemplary implantable medical device of FIG. 1 located in and near a heart.

FIG. 2 is a schematic exemplary representation of IMD 10 as an implanted, two-chamber cardiac pacemaker with bipolar leads. Bipolar, endocardial LV coronary sinus lead 12 is passed through the right atrium 22 of heart 20, into the coronary sinus 24 and then inferiorly in the great vein and cardiac veins extending from coronary sinus 24 to extend the distal bipolar pace/sense electrodes 26 and 28 alongside the LV chamber 30. In this way, pace/sense electrodes 26 and 28 are deployed to sense electrical signals propagating in left ventricle 30 and to deliver pacing pulses to left ventricle 30.

Bipolar, endocardial RV lead 14 is deployed through right atrium 22 into the right ventricle 32 where its distal pace/sense electrodes 34 and 36 sense electrical signals propagating in right ventricle 32 and deliver pacing pulses to right ventricle 32. The distal end of RV lead 14 typically includes a fixation mechanism 38, such as tines or a screw, to anchor the distal end in place proximate to the apex of heart 20. Fixation mechanism 38 may affix to the tissue of right ventricle 32 by, for example, burrowing into the tissue or engaging ventricular trabeculae. In addition, fibrous tissue typically develops following implantation, further anchoring the distal end of RV lead 14.

In some embodiments of the invention, the distal end of LV lead 12 includes no fixation mechanism. In the deployment shown in FIG. 2, LV lead 12 is deployed in a smooth vessel that includes no trabeculae or other structure for anchoring. In addition, the interior of the vessel does not develop fibrous tissue implantation. As a result, it is possible that the engagement between LV tissue and electrodes 26 and 28 may be disturbed. In particular, the distal end of lead 12 may become dislodged, and the electrical stability of the tissue-electrode interface may be adversely affected.

Under ordinary conditions, pace/sense electrodes 26, 28, 34 and 36 sense electrical signals attendant to the depolarization and repolarization of heart 20. The electrical signals are conducted to IMD 10 via leads 12 and 14. Pace/sense electrodes 26, 28, 34 and 36 further deliver pacing pulses for causing depolarization of cardiac tissue in the vicinity of the distal ends thereof. The pacing pulses are generated by IMD 10 and are transmitted to pace/sense electrodes 26, 28, 34 and 36 via leads 12 and 14.

RV lead 14 is formed with an in-line connector 40 fitting into a bipolar bore of connector block 16. RV lead 14 includes a pair of electrically insulated conductors that couple electrodes 34 and 36 to IMD 10. Similarly, LV coronary sinus lead 12 is formed with an in-line connector 42 fitting into a bipolar bore of connector block 16. LV coronary sinus lead 12 couples electrodes 26 and 28 to IMD 10.

IMD 10 delivers pacing pulses to one or both of ventricles 30, 32. During a particular cardiac cycle, IMD 10 may deliver pacing pulses to left ventricle 30 only, to right ventricle 32 only, or to both ventricles. Pacing both ventricles on a cardiac cycle is called "bi-ventricular pacing." When IMD 10 engages in bi-ventricular pacing, the pacing pulses to the two ventricles may be delivered simultaneously, or the pacing pulses may be delivered separated by a time delay.

In general, the invention is directed to techniques by which IMD 10 may automatically change from bi-ventricular pacing to single-ventricle pacing and back to bi-ventricular pacing again. As used herein, "single-ventricle pacing" comprises pacing one ventricle on a cardiac cycle and inhibiting pacing of the other ventricle on the same cardiac cycle.

When a patient first receives an IMD that can perform bi-ventricular pacing, bi-ventricular pacing is typically enabled, and the IMD paces both ventricles. Studies have shown, however, that single-left-ventricle pacing is often as beneficial to the patient, or more beneficial to the patient, as bi-ventricular pacing. Physicians enable bi-ventricular pacing because of the risk of failure or dislodgement of the LV lead. Should the LV lead fail or become dislodged, single-ventricle pacing may fail to pace the heart adequately and the patient may suffer as a result.

The invention provides techniques for pacing as a function of the reliability of LV pacing. When LV pacing is reliable, IMD 10 changes from bi-ventricular pacing to single-ventricle pacing, pacing only left ventricle 30. IMD 10 continues to monitor whether LV pacing is reliable, and may change to bi-ventricular pacing or RV pacing when LV pacing is unreliable. Techniques for determining reliability of LV pacing, and for changing from bi-ventricular pacing to single-ventricle pacing and vice versa, will be discussed below.

The pacing system shown in FIG. 2 is exemplary. The invention is not limited to the electrode placements shown in FIG. 2. Pace/sense electrodes 26, 28, 34 and 36 may be deployed at sites other than those depicted. For example, RV pace/sense electrodes 34 and 36 may be epicardial, rather than endocardial as shown in FIG. 2. The pacing system may also include alternate or additional leads that deploy electrodes elsewhere around ventricles 30, 32, or proximate to the atria for sensing or pacing.

Furthermore, the invention is not limited to application with the bipolar ventricular lead systems depicted in FIG. 2. The invention may be employed with unipolar lead systems that employ a single pace/sense electrode in the depicted positions proximate to right ventricle 32 and left ventricle 30. Unipolar electrodes may cooperate with a remote electrode formed as part of the outer surface of the hermetically sealed housing 18 of IMD 10.

Figure 3:
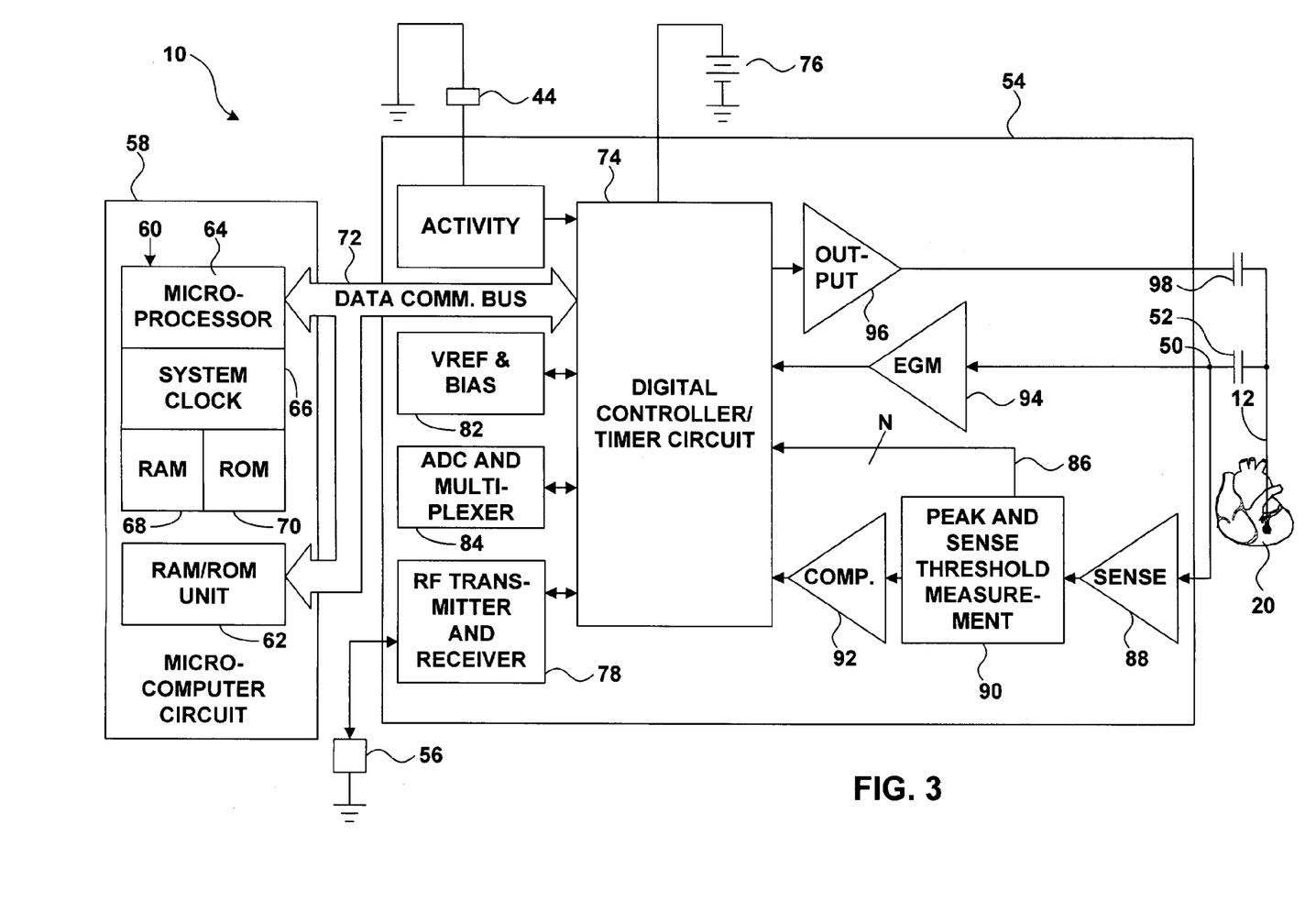
FIG. 3 is a block diagram illustrating the constituent components of the implantable medical device of FIGS. 1 and 2.

FIG. 3 shows a block diagram illustrating the constituent components of IMD 10 in accordance with one embodiment of the present invention. IMD 10 is a pacemaker having a microprocessor-based architecture. For the sake of convenience, IMD 10 in FIG. 3 is shown with LV lead 12 only connected thereto. However, it is understood that similar circuitry and connections not explicitly shown in FIG. 3 apply to RV lead 14 (shown in FIGS. 1 and 2).

As shown in FIG. 3, lead 12 is coupled to node 50 in IMD 10 through input capacitor 52, which is in turn coupled to input/output circuit 54. Also coupled to input/output circuit 54 is activity sensor or accelerometer 44, which may comprise a piezoceramic accelerometer bonded to a hybrid circuit located inside housing 18 (shown in FIGS. 1 and 2). Activity sensor 44 typically (although not necessarily) provides a sensor output that varies as a function of a measured parameter relating to a patient's metabolic requirements. Activity sensor or accelerometer 44 is most preferably attached to a hybrid circuit located inside hermetically sealed housing 18 of IMD 10.

Further coupled to input/output circuit 54 is antenna 56, which facilitates communication with one or more external devices. IMD 10 is programmable by means of an external programming unit (not shown in the figures), which provides a series of encoded signals to IMD 10, typically through a programming head that transmits or telemeters radio-frequency (RF) encoded signals to IMD 10 via antenna 56.

Input/output circuit 54 contains analog circuits for interfacing with heart 20, activity sensor 44, antenna 56 and circuits for the application of stimulating pulses to heart 20. The rate of heart 20 is controlled by hardware—or software-implemented algorithms stored within microcomputer circuit 58.

Microcomputer circuit 58 preferably comprises on-board circuit 60 and off-board circuit 62. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76. For the sake of clarity, the coupling of battery power to the various components of IMD 10 is not shown in the figures.

RF transmitter and receiver telemetry unit 78 coupled to antenna 56 transmits and receives telemetry, which may include data or programming. Programming received via telemetry unit 78 may be stored and executed by microcomputer circuit 58.

VREF and bias circuit 82 generates stable voltage reference and bias currents for analog circuits included in input/output circuit 54. Analog-to-digital converter (ADC) and multiplexer unit 84 digitizes analog signals and voltages to provide, e.g., "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of IMD 10 as well as various refractory, blanking and other timing windows for controlling the operation of peripheral components disposed within input/output circuit 54.

Digital controller/timer circuit 74 is coupled to sensing circuitry, including sense amplifier 88, peak sense and threshold measurement unit 90 and comparator/threshold detector 92. Circuit 74 is further coupled to electrogram (EGM) amplifier 94 for receiving amplified and processed signals sensed by lead 12. The electrogram signal provided by EGM amplifier 94 is employed when, for example, IMD 10 is interrogated by an external programmer to transmit a representation of a cardiac analog electrogram. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92.

Output pulse generator 96 provides amplified pacing stimuli to patient's heart 20 through coupling capacitor 98 in response to a pacing trigger signal provided by digital controller/timer circuit 74 each time either (a) the escape interval times out, (b) an externally transmitted pacing command is received, or (c) in response to other stored commands.

Microcomputer circuit 58 further employs sensing and output circuitry to determine the reliability of LV pacing. Microcomputer circuit 58 may utilize one or more techniques for determining reliability, including impedance testing, capture testing and capture threshold testing. Accordingly, microcomputer circuit 58 and sensing and output circuitry may cooperate to function as impedance measurement circuitry, capture test circuitry and capture threshold testing circuitry. The techniques for determining the reliability of LV pacing will be described in more detail below. Based upon the outcome of testing, microcomputer circuit 58 can determine whether LV pacing is reliable or unreliable. Microcomputer circuit 58 can further control output pulse generator 96 to apply either bi-ventricular pacing or single-ventricle pacing to heart 20 as a function of whether LV pacing is determined to be reliable or unreliable.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 20.

The invention is not limited to IMD 10 shown in FIG. 3 or to any particular component depicted therein. Rather, the invention may be practiced by a variety of implantable devices. For example, the invention may be practiced by an IMD that includes cardioversion and defibrillation functionality, in addition to pacing capability. The invention may also be practiced by a device that paces one or more atria. The invention may further be practiced by a device that includes dedicated impedance measurement circuitry.

Figure 4:
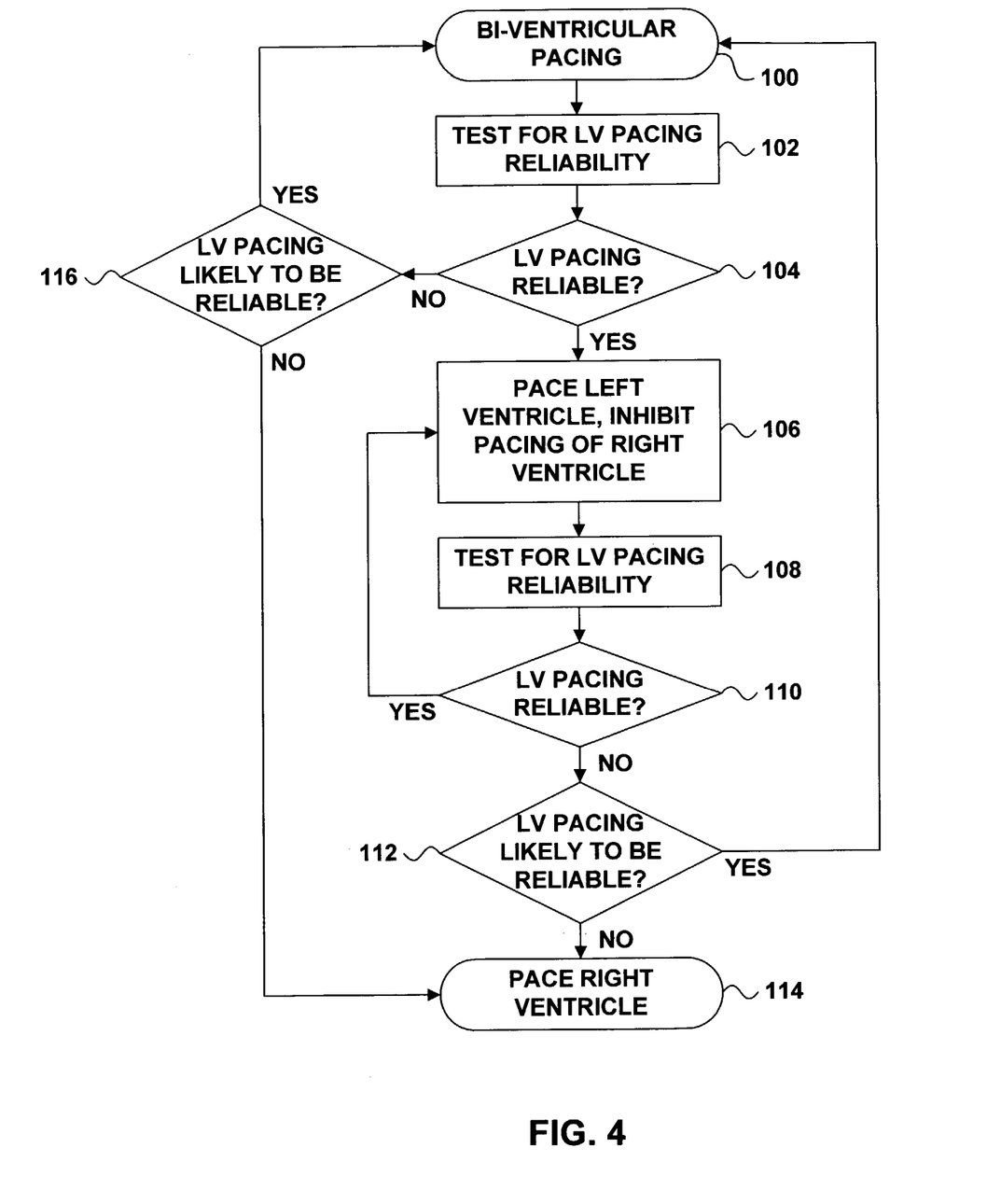
FIG. 4 is a flow diagram illustrating techniques for automatically changing from bi-ventricular pacing to single-ventricle pacing, or vice versa.

FIG. 4 is a flow diagram illustrating techniques for changing from bi-ventricular pacing to single-ventricle pacing and vice versa. As noted above, an IMD may apply bi-ventricular pacing (100) when the IMD is first activated. Bi-ventricular pacing in the early days following implantation serves as a safety measure, because of a risk of failure or dislodgement of the LV lead.

After a period of time has gone by, however, LV pacing may prove to be reliable, and the risk of failure may be less. Accordingly, the IMD tests the reliability of LV pacing (102) using one or more techniques described below. The IMD determines whether pacing of the left ventricle is reliable as a function of an outcome of the testing (104). When the IMD determines that LV pacing is reliable, the IMD changes to single-ventricle pacing, in which the IMD paces the left ventricle and inhibits pacing of the right ventricle (106).

Even though LV pacing is reliable, an event may occur that causes LV pacing to be no longer reliable. One or more LV electrodes may lose fixation with the tissue or otherwise become dislocated, for example, adversely affecting the tissue-electrode interface. As a result, the tissue-electrode interface is no longer stable and pacing at that interface is unreliable. Additional factors that may affect the reliability of LV pacing will be discussed below.

Because LV pacing may be reliable at one time and become unreliable at a later time, the IMD tests the reliability of LV pacing (108) using one or more techniques described below. As long as LV pacing remains reliable (110), IMD applies single-ventricle pacing (106). Should LV pacing become unreliable (110), the IMD may determine whether LV pacing could become reliable at some time in the future (112). For example, IMD may determine whether an electrode that has been dislodged may develop a new tissue-electrode interface. When there is a good possibility that left ventricular pacing may be reliable in the future (112), the IMD may return to bi-ventricular pacing (100). When there is a poor possibility that left ventricular pacing may be reliable in the future (112), the IMD may inhibit LV pacing and pace the right ventricle (114).

When the IMD applies bi-ventricular pacing (100) and tests the reliability of LV pacing (102), it is possible that LV pacing is not reliable and not likely to become reliable (116). When LV pacing is not likely to become reliable, the IMD may abandon LV pacing and pace the right ventricle (114).

In a variation on the techniques depicted in FIG. 4, the IMD may switch from LV pacing to RV pacing when LV pacing is determined to be unreliable, and may periodically apply a LV pace or measure LV lead impedance to determine whether LV pacing may have become reliable.

Figure 5:
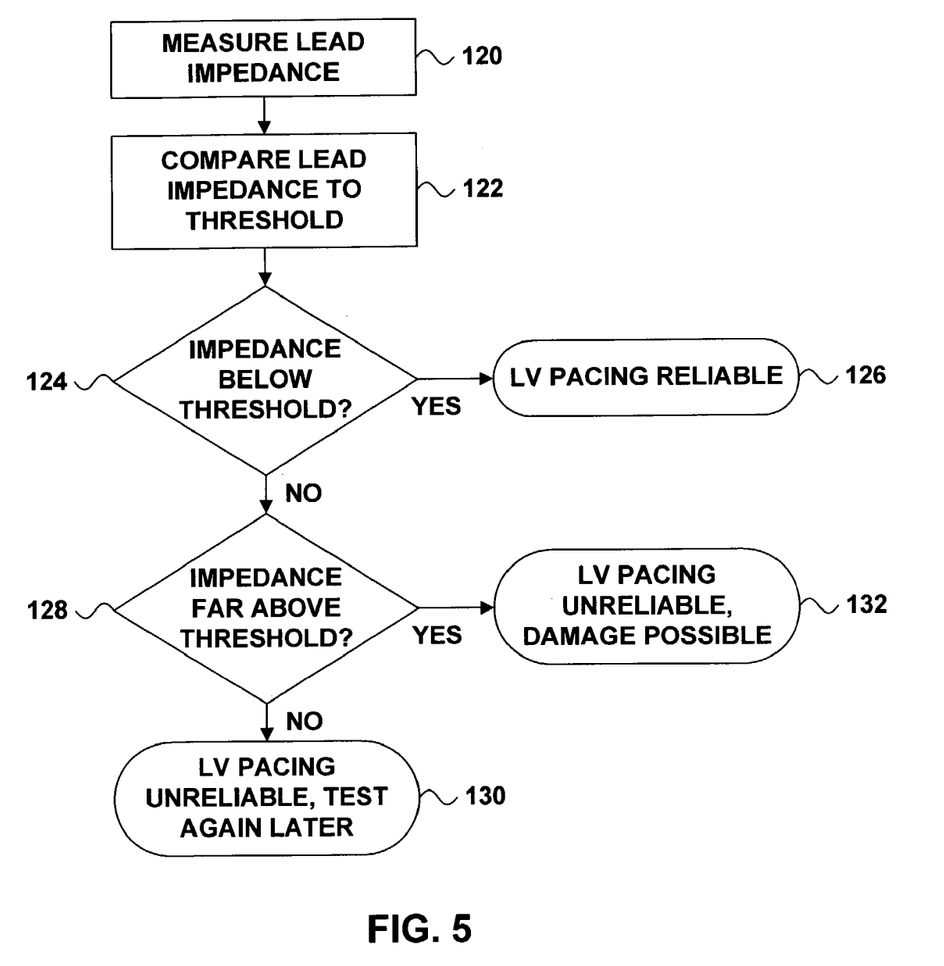
FIG. 5 is a flow diagram illustrating one technique for determining the reliability of LV pacing, using measurement of lead impedance.

FIG. 5 is a flow diagram illustrating a technique for determining whether LV pacing is reliable. The technique involves the IMD measuring an impedance between electrodes to assess the fixation of LV electrodes and the electrical stability of the tissue-electrode interface. In general, a low magnitude of impedance indicates an electrically stable interface. When an LV lead includes bipolar electrodes, such as electrodes 26 and 28 depicted in FIG. 2, the IMD may measure the magnitude of the impedance between the bipolar electrodes. The IMD may measure impedance between other electrodes as well, such as the impedance between an electrode disposed proximate to the left ventricle and an electrode in the housing of the IMD.

The IMD measures the impedance of the LV lead (120). Impedance measurement comprises generating an electrical signal having a known current and measuring the voltage that develops when the current is delivered. Alternatively, impedance measurement comprises generating an electrical signal having a known voltage, and measuring the current that flows between the electrodes. Impedance measurement is used broadly herein to encompass any technique for measuring impedance, or a resistive or reactive component of impedance, or a magnitude or phase of impedance.

The IMD compares the measured impedance to a threshold (122). In general, a low impedance indicates an electrically stable interface, so an impedance measurement below the threshold (124) indicates a good tissue-electrode interface and reliable LV pacing (126). The threshold may be, for example, 3,000 ohms, with impedance magnitudes of approximately 200 to 400 ohms being typical. An impedance measurement above the threshold, but not far above the threshold, (128) indicates a poor tissue-electrode interface and unreliable LV pacing (130). In these circumstances, it may be possible that a pacing electrode will re-lodge at an effective pacing site in the future, thereby re-establishing a tissue-electrode interface and enabling reliable LV pacing. The IMD may use the LV lead for bi-ventricular pacing, and/or may test the LV lead from time to time to determine whether the tissue-electrode interface has been reestablished and LV pacing thereby has become reliable.

An impedance measurement far above the threshold (128), such as one megaohm or above, indicates unreliable LV pacing, and further suggests damage to the lead (132). Serious damage, such as a lead fracture, disrupts the electrical conductors in the lead and makes the electrodes ineffective for sensing and pacing. Where there has been lead damage, it is highly unlikely that the lead can ever supply reliable LV pacing. Accordingly, the IMD may thereafter pace the right ventricle and inhibit LV pacing on a persistent basis.

In addition to or as an alternative to threshold-based comparisons (124, 128) shown in FIG. 5, the IMD may also monitor changes in impedance (not shown in FIG. 5). When the magnitude of an impedance on one cardiac cycle is substantially the same as the magnitude of the impedance in a subsequent cardiac cycle, the IMD may determine that LV pacing is reliable. A substantial change in magnitude of the impedance from one cardiac cycle to another, especially an abrupt increase in magnitude, is indicative of lead dislodgment or lead damage, and may cause the IMD to determine that LV pacing is unreliable. The substantial change in magnitude of the impedance need not be abrupt, however, but may appear after an extended period.

In a variation on the techniques depicted in FIG. 5, the IMD may also determine that LV pacing is unreliable when the magnitude of the impedance is too low. Extremely low impedance, e.g., impedance far below 100 ohms, may indicate shorting, possibly due to lead damage. When the impedance of the LV lead is extremely low, the IMD may pace the right ventricle and inhibit LV pacing on a persistent basis.

Figure 6:
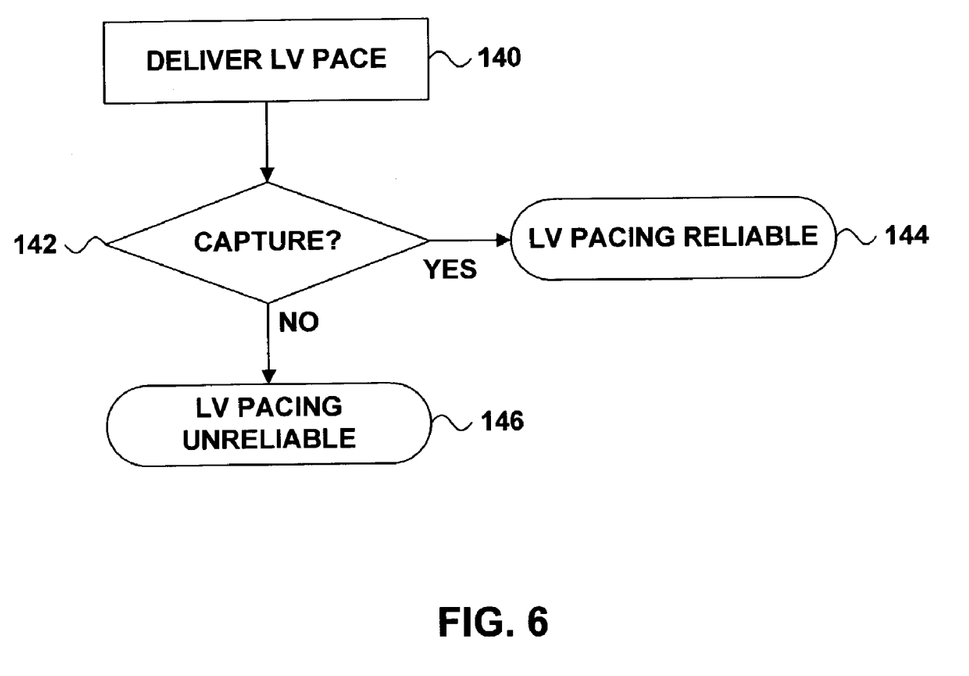
FIG. 6 is a flow diagram illustrating one technique for determining the reliability of LV pacing, using capture testing.

FIG. 6 is a flow diagram illustrating another technique for determining whether LV pacing is reliable. Upon delivery of an LV pace (140), the IMD monitors whether the LV pace captures the left ventricle (142), i.e., whether the pace causes ventricular activation. Successful capture indicates reliable LV pacing (144) and a failure to capture indicates unreliable LV pacing (146). Failure to capture, or intermittent capture, may be an early indication of dislodgment of the LV lead, for example, or damage to the LV lead. When the IMD detects a failure to capture, the IMD may apply other techniques to confirm whether LV pacing is reliable.

Figure 7:
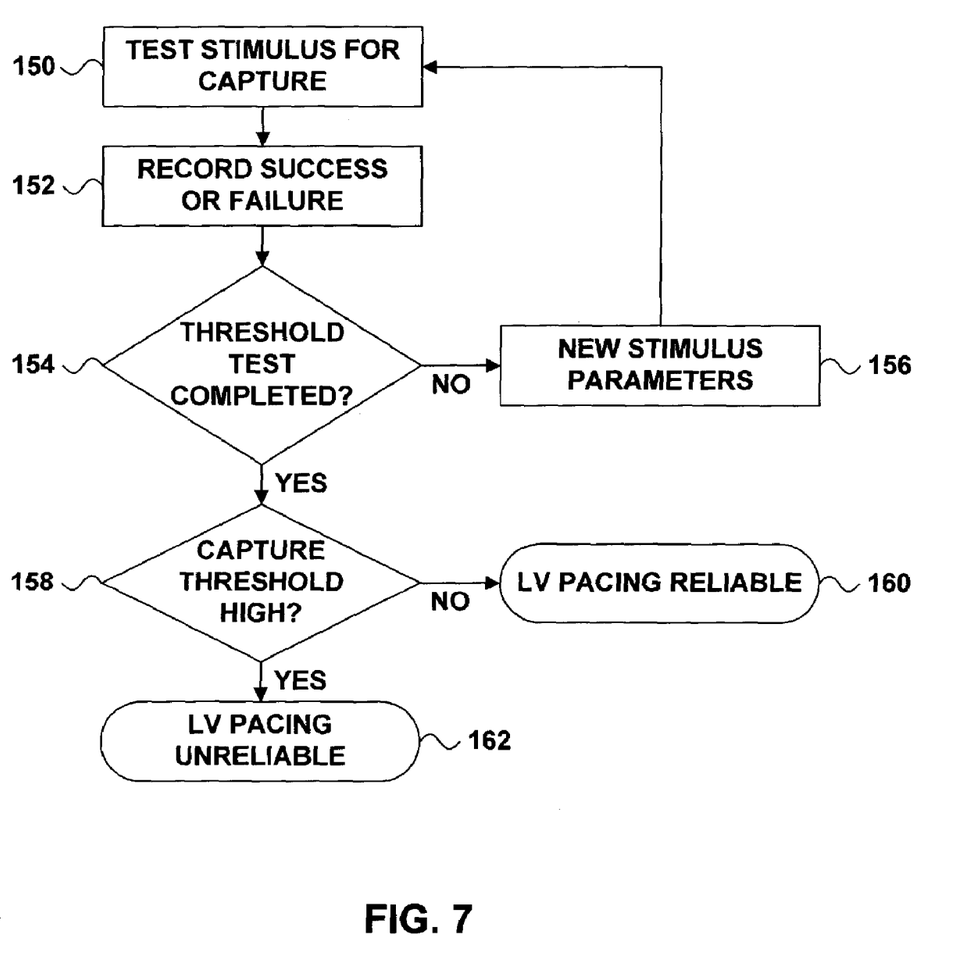
FIG. 7 is a flow diagram illustrating one technique for determining the reliability of LV pacing, using capture threshold testing.

FIG. 7 is a flow diagram illustrating a further technique for determining whether LV pacing is reliable. This technique involves determination of LV pacing reliability with a capture threshold test. In a typical capture threshold test, a pacing stimulus of a known amplitude and duration is applied to the left ventricle, and the IMD monitors whether the pace captures the ventricle (150). The IMD records the success or failure of the pace to capture the ventricle (152). In the event of a failure, the IMD typically delivers a substantially larger ventricular pace (not shown in FIG. 7) to activate the ventricle. A typical capture threshold test involves several test paces as different amplitudes and/or durations (154, 156). Upon completion of the capture threshold test, the IMD has recorded data from which the IMD can determine the characteristics of the smallest pulse or pulses needed to capture the ventricle. These smallest pulses define the "capture threshold."

The IMD determines whether LV pacing is reliable as a function of the capture threshold (158). When the capture threshold is below a predetermined value, such as a predetermined energy threshold (e.g., seven volts at 1 millisecond), LV pacing is reliable (160). When the capture threshold is above the predetermined value, LV pacing is unreliable (162). In a variation on the techniques depicted in FIG. 6, the IMD may also monitor the variation in capture threshold over time. Substantial variation of the capture threshold over time may call into question the stability of the tissue-electrode interface and may indicate that LV pacing is unreliable (162).

The IMD may use any or all of the techniques shown in FIGS. 5-7 to determine whether LV pacing is reliable or unreliable. The invention is not limited to the specific techniques depicted in FIGS. 5-7, however. In some circumstances, an IMD may determine that LV pacing is reliable according to one technique, and apply single-ventricle pacing, even though LV pacing may be determined to be unreliable according to another technique.

A number of embodiments of the invention have been described. However, one skilled in the art will appreciate that the invention can be practiced with embodiments other than those disclosed. For example, the invention may be practiced in devices other than the specific devices described herein, and may implement techniques for determining the reliability of LV pacing other than those that are described herein.

The invention further encompasses inhibiting right ventricular pacing by setting a long interval between the left ventricular pace and the scheduled right ventricular pace. When the left ventricular pace causes ventricular activation, the right ventricular pace is inhibited. When the left ventricular pace fails to cause ventricular activation, however, a scheduled right ventricular pace is applied.

The invention may be embodied as a computer-readable medium that includes instructions for causing a programmable processor, such as microcomputer circuit 58 shown in FIG. 3, to carry out the methods described above. A "computer-readable medium" includes but is not limited to read-only memory, Flash memory and a magnetic or optical storage medium. The instructions may be implemented as one or more software modules, which may be executed by themselves or in combination with other software. These and other embodiments are within the scope of the following claims

The invention claimed is:

1. A method comprising:
 pacing a left ventricle in a first cardiac cycle;
 pacing a right ventricle in the first cardiac cycle;
 determining whether the pacing of the left ventricle is reliable in the first cardiac cycle; and
 pacing the left ventricle in a second cardiac cycle and inhibiting pacing of the right ventricle in the second cardiac cycle when the pacing of the left ventricle is determined to be reliable,
 wherein determining whether the pacing of the left ventricle is reliable comprises:
  testing an impedance of a left ventricular lead in a third cardiac cycle, wherein the third cardiac cycle precedes the first cardiac cycle;
  testing the impedance of the left ventricular lead during the first cardiac cycle; and
  determining that the pacing of the left ventricle is reliable when a magnitude of the impedance in the first cardiac cycle is substantially the same as a magnitude of the impedance in the third cardiac cycle.

2. The method of claim 1, wherein determining whether pacing of the left ventricle is reliable further comprises determining that the pacing of the left ventricle is reliable when the magnitude of the impedance in the first cardiac cycle is below a predetermined value.

3. The method of claim 2, wherein the predetermined value is a first predetermined value, the method further comprising inhibiting pacing of the left ventricle when the magnitude of the impedance in the first cardiac cycle is above a second predetermined value.

4. The method of claim 1, wherein determining whether the pacing of the left ventricle is reliable further comprises testing a capture threshold of the left ventricle.

5. The method of claim 4, wherein determining whether pacing of the left ventricle is reliable comprises determining that the pacing of the left ventricle is reliable when the capture threshold is below a predetermined value.

6. The method of claim 1, wherein determining whether the pacing of the left ventricle is reliable further comprises monitoring whether the pacing of the left ventricle captures the left ventricle.

7. The method of claim 6, wherein determining whether pacing of the left ventricle is reliable comprises determining that the pacing of the left ventricle is reliable when the pacing of the left ventricle captures the left ventricle.

8. The method of claim 1, further comprising:
 determining whether pacing of the left ventricle in the second cardiac cycle is reliable; and
 pacing the right ventricle in a fourth cardiac cycle when the pacing of the left ventricle in the second cardiac cycle is determined to be unreliable.

9. The method of claim 1, wherein the second cardiac cycle is a cardiac cycle that is immediately subsequent to the first cardiac cycle.

10. A method comprising:
 pacing a left ventricle in a first cardiac cycle and inhibiting pacing of a right ventricle in the first cardiac cycle;
 determining whether pacing of the left ventricle is reliable in the first cardiac cycle; and
 pacing the right ventricle in a second cardiac cycle when the pacing of the left ventricle is determined to be unreliable,
 wherein determining whether the pacing of the left ventricle is reliable comprises:
  testing an impedance of a left ventricular lead in a third cardiac cycle, wherein the third cardiac cycle precedes the first cardiac cycle;
  testing the impedance of the left ventricular lead during the first cardiac cycle; and
  determining that the pacing of the left ventricle is reliable when a magnitude of the impedance in the first cardiac cycle is substantiailly the same as a magnitude of the impedance in the third cardiac cycle.

11. The method of claim 10, wherein determining whether pacing of the left ventricle is reliable further comprises testing a capture threshold of the pacing of the left ventricle.

12. The method of claim 10, wherein determining whether pacing of the left ventricle is reliable further comprises monitoring whether the pacing of the left ventricle captures the left ventricle.

13. The method of claim 10, further comprising pacing the left ventricle in the second cardiac cycle.

14. The method of claim 13, further comprising:
 determining whether pacing of the left ventricle is reliable in the second cardiac cycle; and
 pacing the left ventricle in a fourth cardiac cycle and inhibiting pacing of the right ventricle in the fourth cardiac cycle when the pacing of the left ventricle is determined to be reliable in the second cardiac cycle.

15. The method of claim 10, wherein the second cardiac cycle is a cardiac cycle that is immediately subsequent to the first cardiac cycle.

16. A computer-readable medium comprising instructions for causing a programmable processor to:
- pace a left ventricle in a first cardiac cycle and pace a right ventricle in the first cardiac cycle;
- determine whether the pacing of the left ventricle is reliable in the first cardiac cycle; and
- pace the left ventricle in a second cardiac cycle and inhibit pacing of the right ventricle in the second cardiac cycle when the pacing of the left ventricle is determined to be reliable,
- wherein the instructions causing the processor to determine whether the pacing of the left ventricle is reliable comprise instructions for causing the processor to:
  - test an impedance of a left ventricular lead in a third cardiac cycle, wherein the third cardiac cycle precedes the first cardiac cycle;
  - test the impedance of the left ventricular lead during the first cardiac cycle; and
  - determine that the pacing of the left ventricle is reliable when a magnitude of the impedance in the first cardiac cycle is substantially the same as a magnitude of the impedance in the third cardia cycle.

17. The medium of claim 16, wherein the instructions causing the processor to determine whether pacing of the left ventricle is reliable further comprise instructions causing the processor to determine that the pacing of the left ventricle is reliable when the magnitude of the impedance in the first cardiac cycle is below a predetermined value.

18. The medium of claim 17, wherein the predetermined value is a first predetermined value, the instructions further causing the processor to inhibit pacing of the left ventricle when the magnitude of the impedance in the first cardiac cycle is above a second predetermined value.

19. The medium of claim 16, wherein the instructions causing the processor to determine whether the pacing of the left ventricle is reliable further comprise instructions causing the processor to test a capture threshold of the left ventricle.

20. The medium of claim 19, wherein the instructions causing the processor to determine whether pacing of the left ventricle is reliable comprise instructions causing the processor to determine that the pacing of the left ventricle is reliable when the capture threshold is below a predetermined value.

21. The medium of claim 16, wherein the instructions causing the processor to determine whether the pacing of the left ventricle is reliable further comprise instructions causing the processor to monitor whether the pacing of the left ventricle captures the left ventricle.

22. The medium of claim 21, wherein the instructions causing the processor to determine whether pacing of the left ventricle is reliable comprise instructions causing the processor to determine that the pacing of the left ventricle is reliable when the pacing of the left ventricle captures the left ventricle.

23. The medium of claim 16, the instructions further causing the processor to:
- determine whether pacing of the left ventricle is reliable in the second cardiac cycle; and
- pace the right ventricle in a fourth cardiac cycle when the pacing of the left ventricle in the second cardiac cycle is determined to be unreliable.

24. The medium of claim 16, wherein the second cardiac cycle is a cardiac cycle that is immediately subsequent to the first cardiac cycle.

25. A computer-readable medium comprising instructions for causing a programmable processor to:
- pace a left ventricle in a first cardiac cycle and inhibit pacing of a right ventricle in the first cardiac cycle;
- determine whether pacing of the left ventricle is reliable in the first cardiac cycle; and
- pace the right ventricle in a second cardiac cycle when the pacing of the left ventricle is determined to be unreliable,
- wherein the instructions causing the processor to determine whether the pacing of the left ventricle is reliable comprise instructions for causing the processor to:
  - test an impedance of a left ventricular lead in a third cardiac cycle, wherein the third cardiac cycle precedes the first cardiac cycle;
  - test the impedance of the left ventricular lead during the first cardiac cycle; and
  - determine that the pacing of the left ventricle is reliable when a magnitude of the impedance in the first cardia cycle is substantially the same as a magnitude of the impedance in the third cardiac cycle.

26. The medium of claim 25, wherein the instructions causing the processor to determine whether the pacing of the left ventricle is reliable further comprise instructions causing the processor to test a capture threshold of the pacing of the left ventricle.

27. The medium of claim 25, wherein the instructions causing the processor to determine whether the pacing of the left ventricle is reliable further comprise instructions causing the processor to monitor whether the pacing of the left ventricle captures the left ventricle.

28. The medium of claim 25, the instructions further causing the processor to pace the left ventricle in the second cardiac cycle.

29. The medium of claim 28, the instructions further causing the processor to:
- determine whether pacing of the left ventricle is reliable in the second cardiac cycle; and
- pace the left ventricle in a fourth cardiac cycle and inhibit pacing of the right ventricle in the fourth cardiac cycle when the pacing of the left ventricle is determined to be reliable in the second cardiac cycle.

30. The medium of claim 25, wherein the second cardiac cycle is a cardiac cycle that is immediately subsequent to the first cardiac cycle.

31. A device comprising:
- a left ventricular lead having at least one left ventricular electrode deployed proximate to a left ventricle of a heart;
- a right ventricular lead having at least one right ventricular electrode deployed proximate to a right ventricle of the heart;
- a pulse generator to generate at least one pacing stimulus to pace at least one of the left ventricle via the left ventricular electrode and the right ventricle via the right ventricular electrode;
- impedance measurement circuitry to test an impedance of the left ventricular lead, and
- a processor to determine whether a pacing of the left ventricle is reliable as a function of the outcome of the impedance test and to control the pulse generator to apply one of bi-ventricular pacing and single-ventricle pacing as a function of the determination,
- wherein the impedance test comprises:
  - testing the impedance of the left ventricular lead in a third cardiac cycle, wherein the third cardiac cycle precedes a first cardiac cycle; and testing the impedance of the left ventricular lead during the first cardiac cycle, and wherein the processor is further configured to determine that the pacing of the left ventricle is reliable when a magnitude of the impedance in the first cardiac cycle is substantially the same as a magnitude of the impedance in the third cardiac cycle.

32. The device of claim 31, wherein the processor is further configured to control the pulse generator to pace the left ventricle in a first cardiac cycle and to pace the right ventricle in the first cardiac cycle, and to control the pulse generator to pace the left ventricle in a second cardiac cycle and to inhibit pacing of the right ventricle in the second cardiac cycle when the processor determines that the pacing of the left ventricle is reliable.

33. The device of claim 31, wherein the processor is further configured to control the pulse generator to pace the left ventricle in a first cardiac cycle and to inhibit pacing of the right ventricle in the first cardiac cycle, and to control the pulse generator to pace the left ventricle in a second cardiac cycle and to pace of the right ventricle in the second cardiac cycle when the processor determines that the pacing of the left ventricle is unreliable.

34. The device of claim 31, further comprising capture test circuitry to test whether a pace applied by the left ventricular lead captures the left ventricle, wherein the processor is further configured to determine whether the pacing of the left ventricle is reliable as a function of an outcome of the test.

35. The device of claim 31, further comprising capture threshold testing circuitry to test a capture threshold for the left ventricle, wherein the processor is further configured to determine whether the pacing of the left ventricle is reliable as a function of an outcome of the test.

\* \* \* \* \*